US00PP22177P2

(12) United States Plant Patent
Podaras

(10) Patent No.: US PP22,177 P2
(45) Date of Patent: Oct. 4, 2011

(54) ***BUDDLEJA* PLANT NAMED 'PODARAS #13'**

(50) Latin Name: *(Buddleja davidii×Buddleja alternifolia)×Buddleja davidii*
Varietal Denomination: Podaras #13

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,669

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

(56) References Cited

OTHER PUBLICATIONS

*Buddleja* named 'Flutterby Petite Tutti Fruitt Pink' http://www.ballhort.com/Nursery/plant_info (retrieved from website Mar. 17, 2011) (2 pages).*

* cited by examiner

*Primary Examiner* — Susan McCormick Ewoldt
(74) *Attorney, Agent, or Firm* — C. A. Whealy

(57) ABSTRACT

A new and distinct cultivar of *Buddleja* plant named 'Podaras #13', characterized by its compact, upright and outwardly spreading plant habit; freely flowering habit; sterile purple violet-colored flowers; and good garden performance.

1 Drawing Sheet

Botanical designation: (*Buddleja davidii×Buddleja alternifolia*)×*Buddleja davidii.*
Cultivar denomination: 'PODARAS #13 '.

BACKGROUND OF THE INVENTION

The present invention relates to a new and distinct cultivar of *Buddleja* plant, botanically known as (*Buddleja davidii×Buddleja alternifolia*)×*Buddleja davidii* and hereinafter referred to by the name 'Podaras #13'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Mar. 3, 2006 in Ithaca, N.Y., of an unnamed selection of *Buddleja davidii×Buddleja alternifolia*, not patented, as the female, or seed, parent with an unnamed selection of *Buddleja davidii*, not patented, as the male, or pollen, parent. The new *Buddleja* plant was discovered and selected by the Inventor as a single flowering plant within the progeny of the stated cross-pollination in a controlled environment in Ithaca, N.Y. in August, 2007.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #13'. These characteristics in combination distinguish 'Podaras #13' as a new and distinct *Buddleja* plant:

1. Compact, upright and outwardly spreading plant habit.
2. Freely flowering habit.
3. Sterile purple violet-colored flowers.
4. Good garden performance.

Plants of the new *Buddleja* differ from plants of the female parent selection in the following characteristics:

1. Plants of the new *Buddleja* are smaller and denser than plants of the female parent selection.
2. Plants of the new *Buddleja* and the female parent selection differ in flower color as plants of the female parent selection have dark pink-colored flowers with white-colored centers.

Plants of the new *Buddleja* differ from plants of the male parent selection in the following characteristics:

1. Plants of the new *Buddleja* are compact and denser than plants of the male parent selection.
2. Plants of the new *Buddleja* and the male parent selection differ in flower color as plants of the male parent selection have deep purple-colored flowers with white-colored centers.

Plants of the new *Buddleja* can be compared to plants of *Buddleja davidii* 'Pink Delight', not patented. In side-by-side comparisons, plants of the new *Buddleja* and 'Pink Delight' differed in the following characteristics:

1. Plants of the new *Buddleja* were shorter and more compact than plants of 'Pink Delight'.
2. Leaves of plants of the new *Buddleja* were more rounded than leaves of plants of 'Pink Delight'.
3. Plants of the new *Buddleja* and 'Pink Delight' differed in flower color as plants of 'Pink Delight' had pink-colored flowers.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #13' grown in a container.

The photograph at the top of the sheet is a close-up view of a typical inflorescence of 'Podaras #13'.

DETAILED BOTANICAL DESCRIPTION

The aforementioned photographs and following observations, measurements and values describe plants grown in Arroyo Grande, Calif. under commercial practice during the summer in 12.5-cm containers in a polyethylene-covered greenhouse with day temperatures averaging 21° C. and night temperatures averaging 7° C. Plants were pinched two times and were four months old when the photographs and description were taken. In the following description, color references are made to The Royal Horticultural Society Colour Chart, 2007 Edition, except where general terms of ordinary dictionary significance are used.

Botanical classification: (*Buddleja davidii*×*Buddleja alternifolia*)×*Buddleja davidii* 'Podaras #13'.

Parentage:

*Female, or seed, parent*—Unnamed selection of *Buddleja davidii*×*Buddleja alternifolia*, not patented.

*Male, or pollen, parent.*—Unnamed selection of *Buddleja davidii*, not patented.

Propagation:

*Type.*—By cuttings.

*Time to initiate roots plant, summer.*—About two weeks at temperatures of 18° C. to 24° C.

*Time to initiate roots plant, winter.*—About two to three weeks at temperatures of 18° C. to 24° C.

*Time to produce a rooted plant, summer.*—About three weeks at temperatures of 18° C. to 24° C.

*Time to produce a rooted plant, winter.*—About three to four weeks at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; compact, upright and outwardly spreading habit; broad inverted triangle; vigorous growth habit.

*Plant height.*—About 25 cm.

*Plant width* (*spread*).—About 24 cm by 30 cm.

*Lateral branches.*—Quantity: About eight main branches per plant. Length: About 25 cm. Diameter: About 4 mm. Internode length: About 2.5 cm to 3.5 cm. Strength: Strong. Texture, developing stems: Tomentose. Texture, mature stems: Smooth, glabrous. Color, developing: Close to 147C. Color, mature: Close to N199C.

Foliage description:

*Arrangement.*—Opposite, simple.

*Length.*—About 4.8 cm.

*Width.*—About 1.7 cm.

*Shape.*—Elliptical.

*Apex.*—Acute.

*Base.*—Attenuate.

*Margin.*—Serrulate.

*Texture, upper surface.*—Smooth, glabrous.

*Texture, lower surface.*—Lanulose.

*Venation pattern.*—Pinnate, reticulate.

*Color.*—Developing leaves, upper surface: Close to 137A. Developing leaves, lower surface: Close to N138C. Fully expanded leaves, upper surface: Close to N137B; venation, close to 137B. Fully expanded leaves, lower surface: Close to 148B; venation, close to 191C.

*Petiole.*—Length: About 5 mm. Diameter: About 1 mm. Texture, upper and lower surfaces: Pubescent. Color, upper and lower surfaces: Close to 146D.

Flower description:

*Flower type/habit.*—Single rotate and salverform flowers arranged in compound terminal panicles; flowers face upright and outward; panicles roughly conical in shape; freely flowering habit with about 280 flower buds and flowers developing per inflorescence.

*Fragrance.*—None detected.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 1.1 cm. Diameter: About 2.5 mm. Shape: Oblong. Color: Close to 83B.

*Inflorescence height.*—About 6.6 cm.

*Inflorescence diameter.*—About 4 cm.

*Flower diameter.*—About 1 cm.

*Flower depth.*—About 1.2 cm.

*Flower throat, diameter.*—About 2 mm.

*Flower tube, length.*—About 9 mm.

*Flower tube, diameter at base.*—About 1.5 mm.

*Petals.*—Quantity per flower: Typically four in a single whorl; petals fused into a narrow tube. Lobe length: About 4 mm. Lobe width: About 3 mm. Lobe shape: Roughly spatulate. Lobe apex: Rounded. Lobe margin: Erosulate, slightly crinkled. Texture, upper and lower lobe surfaces: Smooth, glabrous. Texture, throat: Slightly pubescent. Texture, tube: Smooth, glabrous. Color: Developing petals, upper surface: Close to N81A. Developing petals, lower surface: Close to N82A. Fully expanded petals, upper surface: Close to N81A; towards the throat, close to 8C; venation, close to N81A; color becoming closer to N81B with development. Fully expanded petals, lower surface: Close to N87B; venation, close to N87B. Throat: Close to N170B, venation, close to N170B. Tube: Close to N70B; venation, close to N70B.

*Sepals.*—Quantity per flower: Typically four in a single whorl, fused towards the base; campanulate calyx. Length: About 1.5 mm. Width: About 1 mm. Shape: Lanceolate. Apex: Acute. Margin: Entire. Texture, upper surface: Smooth, glabrous. Texture, lower surface: Pubescent. Color, upper surface: Close to 146B. Color, lower surface: Close to 147C.

*Peduncles.*—Length: About 2.5 cm. Diameter: About 2 mm. Angle: Mostly erect. Strength: Strong. Texture: Lanulose. Color: Close to 191B.

*Pedicels.*—Length: About 2 mm. Diameter: About 1 mm. Angle: About 45° from peduncle axis. Strength: Moderately strong. Texture: Pubescent. Color: Close to 194B.

*Reproductive organs.*—Stamens: Quantity per flower: Typically four; filaments adnate to the corolla tube. Filament length: About 3 mm. Filament color: Close to 14C. Anther shape: Lanceolate. Anther length: About 1 mm. Anther color: Close to 195C. Pollen amount: None. Pistils: Quantity per flower: One. Pistil length: About 4 mm. Stigma shape: Oval. Stigma color: Close to N186C. Style length: About 1 mm. Style color: Close to 146C. Ovary color: Close to 146D.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja.*

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #13' as illustrated and described.

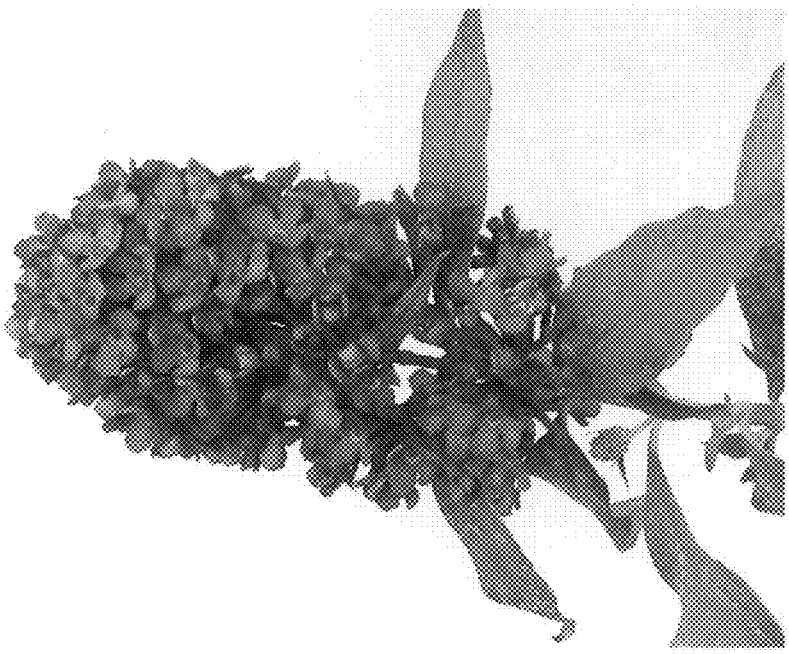
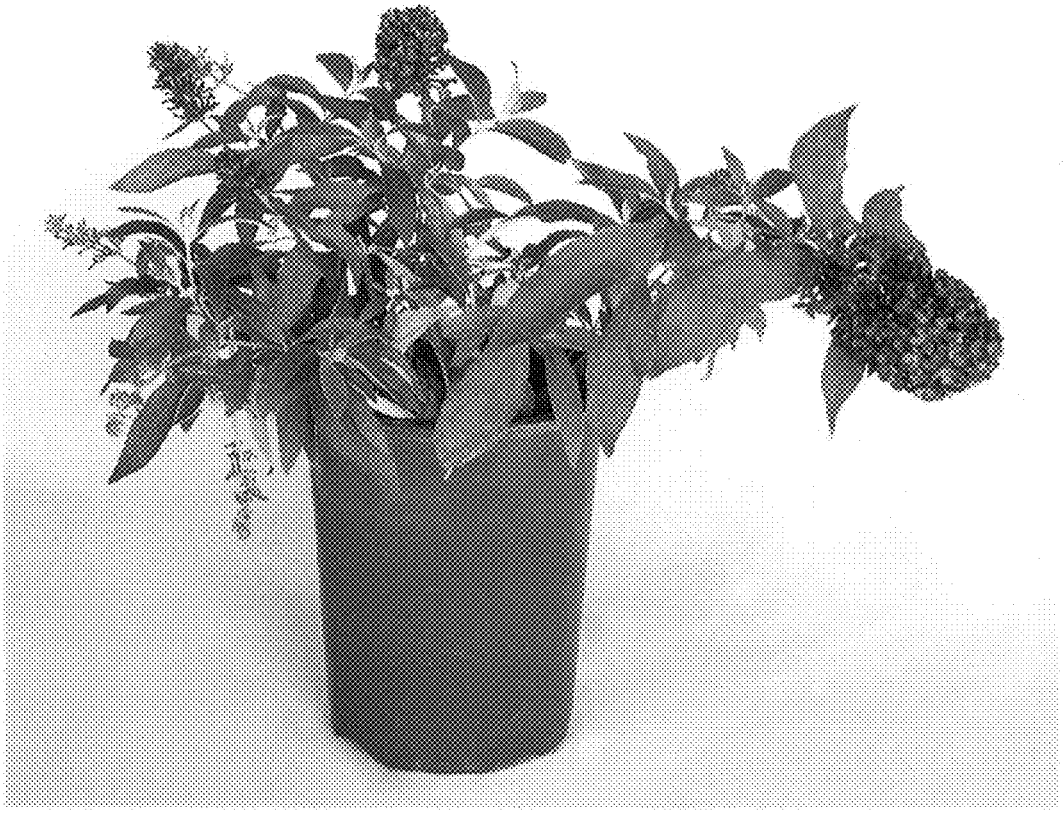

* * * * *